(12) United States Patent
Maymon et al.

(10) Patent No.: US 9,884,120 B2
(45) Date of Patent: Feb. 6, 2018

(54) FLAVOR MODIFYING COMPOSITION, USES THEREOF AND PRODUCTS COMPRISING THE SAME

(71) Applicant: UNAVOO FOOD TECHNOLOGIES LTD, Tel Aviv (IL)

(72) Inventors: Yuval Maymon, Rehovot (IL); Avner Gordin, Bizaron (IL); Jeff Cohen, Long Branch, NJ (US); Jack Dweck, New Rochelle, NY (US)

(73) Assignee: UNAVOO FOOD TECHNOLOGIES LTD, Tel Aviv (IL)

( * ) Notice: Subject to any disclaimer, the term of this patent is extended or adjusted under 35 U.S.C. 154(b) by 0 days.

(21) Appl. No.: 15/182,027

(22) Filed: Jun. 14, 2016

(65) Prior Publication Data

US 2016/0295890 A1    Oct. 13, 2016

Related U.S. Application Data

(63) Continuation of application No. PCT/IL2015/050907, filed on Sep. 8, 2015.

(30) Foreign Application Priority Data

Sep. 8, 2014 (IL) .......................................... 234525

(51) Int. Cl.

| | |
|---|---|
| A23C 9/13 | (2006.01) |
| A23L 2/02 | (2006.01) |
| A23L 2/60 | (2006.01) |
| A61Q 11/00 | (2006.01) |
| A61K 9/08 | (2006.01) |
| A61K 47/46 | (2006.01) |
| A61K 9/00 | (2006.01) |
| A61K 8/97 | (2017.01) |
| A61K 47/26 | (2006.01) |
| A61K 47/42 | (2017.01) |
| A61K 8/60 | (2006.01) |
| A61K 8/64 | (2006.01) |
| A61K 8/00 | (2006.01) |
| A23L 2/56 | (2006.01) |
| A23L 29/25 | (2016.01) |
| A23L 27/00 | (2016.01) |
| A23L 27/30 | (2016.01) |
| A23C 9/156 | (2006.01) |

(52) U.S. Cl.
CPC .......... A61K 47/26 (2013.01); A23C 9/1307 (2013.01); A23C 9/156 (2013.01); A23L 2/02 (2013.01); A23L 2/56 (2013.01); A23L 2/60 (2013.01); A23L 27/36 (2016.08); A23L 27/86 (2016.08); A23L 29/25 (2016.08); A61K 8/602 (2013.01); A61K 8/645 (2013.01); A61K 8/97 (2013.01); A61K 9/0053 (2013.01); A61K 9/08 (2013.01); A61K 47/42 (2013.01); A61K 47/46 (2013.01); A61Q 11/00 (2013.01); A23C 2240/15 (2013.01); A23V 2002/00 (2013.01)

(58) Field of Classification Search
None
See application file for complete search history.

(56) References Cited

U.S. PATENT DOCUMENTS

| | | | | |
|---|---|---|---|---|
| 2002/0192355 | A1* | 12/2002 | Serpelloni | A23L 33/21 426/658 |
| 2004/0058050 | A1* | 3/2004 | Guo | A23L 2/60 426/615 |
| 2008/0311265 | A1* | 12/2008 | MacDonald | A23L 2/39 426/534 |
| 2009/0258129 | A1 | 10/2009 | Sablosky | |
| 2013/0209643 | A1 | 8/2013 | Kruger | |
| 2014/0212562 | A1 | 7/2014 | Daniel | |
| 2015/0208671 | A1* | 7/2015 | Schmidt | A21D 2/36 426/622 |

FOREIGN PATENT DOCUMENTS

| | | | |
|---|---|---|---|
| CN | 102697022 A | * 10/2012 | |
| EP | 2 340 719 A1 | 7/2011 | |
| JP | 2000166506 A | * 6/2000 | |
| WO | 00/74501 A1 | 12/2000 | |
| WO | 2006/095366 A1 | 9/2006 | |
| WO | WO 2006095366 A1 | * 9/2006 | A23L 29/25 |

OTHER PUBLICATIONS

Machine Translation of CN 102697022 A, supplied by Espacenet-Google.*
Kenji Mizutani and Osamu Tanaka, "Use of Stevia rebaudiana sweeteners in Japan", in "Stevia", Chapter 9, Edited by A.Douglas Kinghorn, London: Taylor & Francis, copyright 2002, pp. 178-195.*
S.M. Savita, K. Sheela, Sharan Sunanda, A.G. Shankar and Parama Ramakrishna. Stevia rebaudiana—A Functional Component for Food Industry. J. Hum. Ecol., 15(4): 261-264 (2004).*
Machine translation to English of JP2000166506.*
"Bifidogenic" in the Oxford Dictionary of Food and Nutrition (downloaded Jan. 27, 2017, from http://www.oxfordreference.com/view/10.1093/acref/9780199234875.001.0001/acref-9780199234875-e-5991?rskey=qlgjeR&result=822).*
Altenative Sweeteners, 3rd Edition, Edited by Lyn O'Brien Nabors. New York: Marcel Dekker, 2001, p. 3.*

* cited by examiner

Primary Examiner — Frederick Krass
Assistant Examiner — Michael P Cohen
(74) Attorney, Agent, or Firm — Vorys, Sater, Seymour and Pease LLP

(57) ABSTRACT

Provided is a flavor modifying composition including a blend of a water soluble filler including plant fibers; and at least one sucrose substitute of natural source, wherein said flavor modifying composition includes at least 90% w/w of the filler, the amount being determined when said composition is in dry form; and said flavor modifying composition is water soluble. The flavor modifying composition is particularly effective in enhancing sweet taste and/or aroma of a product. Further provided are products including the flavor modifying composition.

21 Claims, 5 Drawing Sheets

US 9,884,120 B2

FLAVOR MODIFYING COMPOSITION, USES THEREOF AND PRODUCTS COMPRISING THE SAME

This is a Continuation Application of PCT/IL2015/050907, filed on Sep. 8, 2015, an application claiming the benefit under 35 U.S.C. § 119 of Israeli Patent Application No. 234525, filed on Sep. 8, 2014, the content of each of which is hereby incorporated by reference in their entirety.

TECHNOLOGICAL FIELD

The present invention relates to flavor modifying compositions.

BACKGROUND ART

References considered to be relevant as background to the presently disclosed subject matter are listed below
EP 2,340,719;
WO 00/74501.
Acknowledgement of the above reference herein is not to be inferred as meaning that it is in any way relevant to the patentability of the presently disclosed subject matter.

BACKGROUND

Sweet-tasting food products have been demanded by consumers for many years. Such sweet-tasting products include soft drinks, carbonated beverages, gums, confectionaries, candies, snack foods, dairy products, puddings, cereals, bakery products and the like. Nonetheless, the sweetness required for such products usually is based on natural, high calorie sweeteners, such as sucrose (table sugar), fructose, corn syrup, etc.

In addition, attempts were made to develop low-sugar content sucrose-substituted sweetener. Some alternative sweeteners include Sucralose (produced by the substitution of three of the hydroxyl groups in sucrose with chlorine) and *Stevia* (sugar substitute produced from the extract of *Stevia Rebaudiana*), are highly intensive sweeteners, but in the amounts needed for adequate sweetening of foodstuff, such sweeteners exhibit bitter aftertaste, lingering sweetness and astringent palatability. To mask the taste, at times, the artificial sweeteners are combined with other calorie-containing carbohydrates such as dextrose or maltodextrin. The calorie content of *Stevia* blend may reach 3.75 kilocalories per gram, depending on type of blend.

European Patent No. 2,340,719 describes an aroma composition and method for reducing or suppressing an unpleasant taste effect comprising: (i) a sweetener, (ii) ortho-coumaric acid, and optionally (iii) a bitter-masking aroma substance including their physiologically tolerated salts and optionally (iv) an additional aroma substance which is a sweetness intensifying aroma substance and (v) an inactive substance or carrier such as maltodextrin, starches, natural or synthetic polysaccharides and/or vegetable gums such as modified starch or gum Arabic, solvents permitted for aroma compositions such as for example ethanol, propylene glycol, water, glycerine, triacetine, vegetable oil triglycerides, colorants, for example permitted food colourings, colouring vegetable extracts, stabilizers, preservatives, antioxidants and viscosity modifiers. The publication emphasizes on the use of ortho-coumaric acid to reduce or suppress an unpleasant taste effect of a sweetener.

WO 00/74501 describes a particulate fiber composition comprising a first dietary fiber, encapsulated in a coating comprising an insoluble dietary fiber, wherein the encapsulated coating thereby prevents dissolution of the first dietary fiber composition until contact with the gastric juice.

General Description

The present disclosure provides, in accordance with a first of its aspects, a flavor modifying composition comprising a blend of:
(i) water soluble filler comprising plant fibers; and
(ii) at least one sucrose substitute of natural source,
wherein
said flavor modifying composition comprises at least 90% w/w of the filler, the amount being determined when said composition is in dry form;
said flavor modifying composition is water soluble.

It has been surprisingly found that the filler within the flavor modifying composition as disclosed herein was able to mask unpleasant aftertaste of the at least one sucrose substitute of natural source, the masking by the plant derived filler was determined by a blind tasting test using a taste score between 1 to 5, 1 being most unpleasant aftertaste, where 1 gr of said flavor modifying composition is dissolved in 180 ml water at room temperature to obtain dissolved composition and the taste of the dissolved composition is compared by at least one individual to a reference taste score of a same amount of the at least one sucrose substitute of natural source dissolved in 180 ml water at room temperature in the absence of said filler.

In one specific embodiment, the flavor modifying composition is a sweetening composition. Accordingly, the present disclosure also provides a sweetening composition comprising a blend of:
(i) water soluble filler comprising plant fibers; and
(ii) at least one sucrose substitute of natural source,
wherein
said sweetening composition comprises at least 90% w/w of the filler, the amount being determined when said composition is in dry form;
said sweetening composition is water soluble.

In some embodiments, the water soluble filler comprising plant fibers comprises *Acacia* fibers. In some embodiments, the *Acacia* fibers comprise at least fiber gum B and further within some embodiments, when more than one type of fibers are included, at least 50% of fiber gum B.

In some embodiments, the at least one sucrose substitute of natural source is derived from *Stevia*.

Also provided by the present disclosure is the use of a flavor modifying composition as disclosed herein, for the preparation of an oral product.

In addition, provided by the present disclosure is the flavor modifying composition for use as a flavor modifying agent, with particular use as a sweetener.

Finally, provided by the present disclosure is an oral product comprising the flavor modifying composition disclosed herein.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
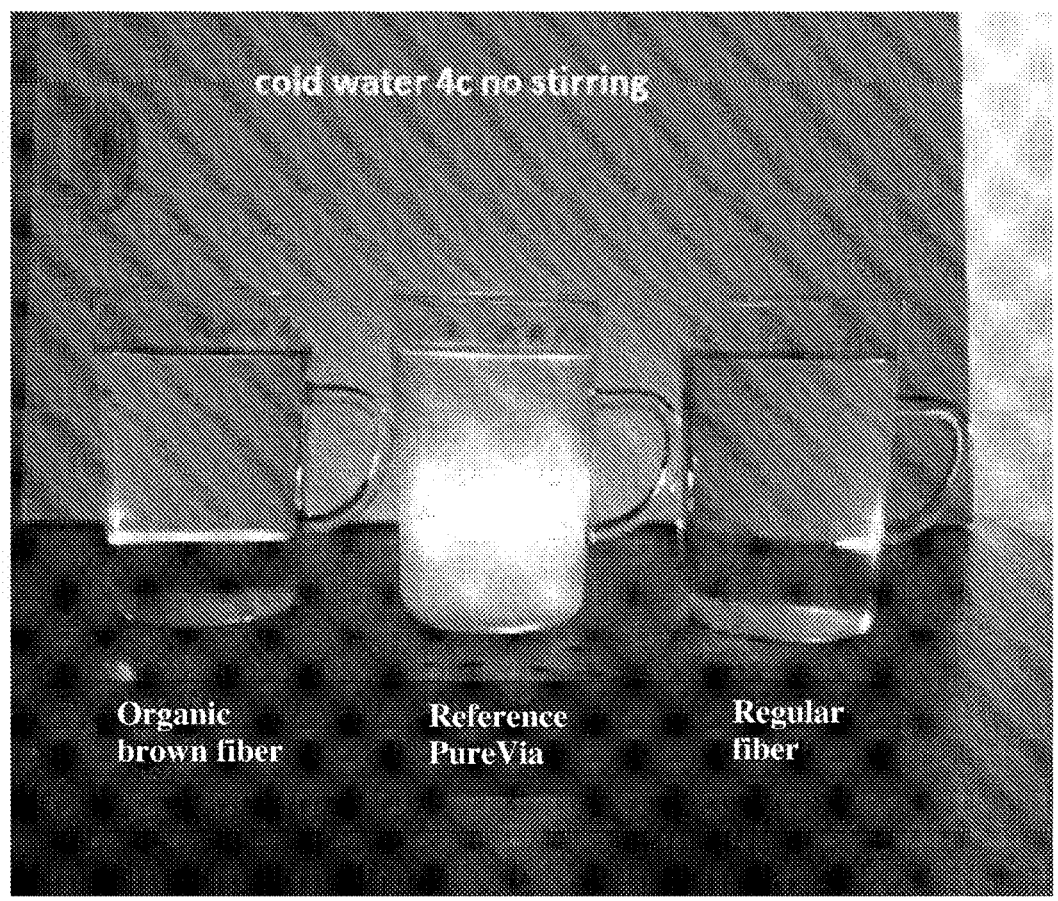
FIG. 1 provides an image of three cups comprising water into which compositions comprising *Acacia* fiber and *Stevia* were introduced at 4° C. (cold water) without stirring; Left cup comprising water and a composition comprising organic brown *Acacia* fiber and *Stevia*, Center cup comprising water into which the commercial PureVia® was mixed, and Right cup comprising water and a composition comprising regular (white) *Acacia* fiber and *Stevia* according to an embodiment of the present disclosure.
Figure 2:
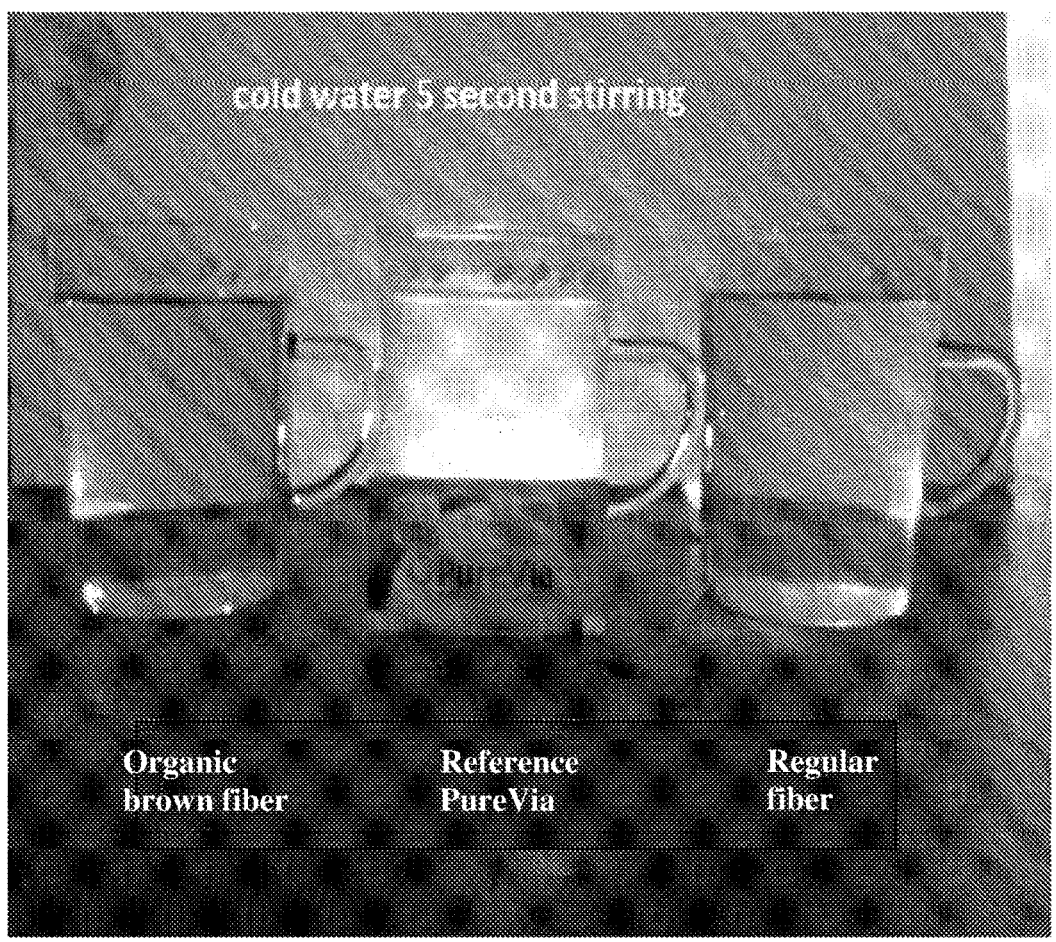
FIG. 2 provides an image of three cups comprising the same compositions as in FIG. 1, albeit this time the introduction of each of the compositions to cold water was followed by mixing for 5 seconds.
Figure 3:
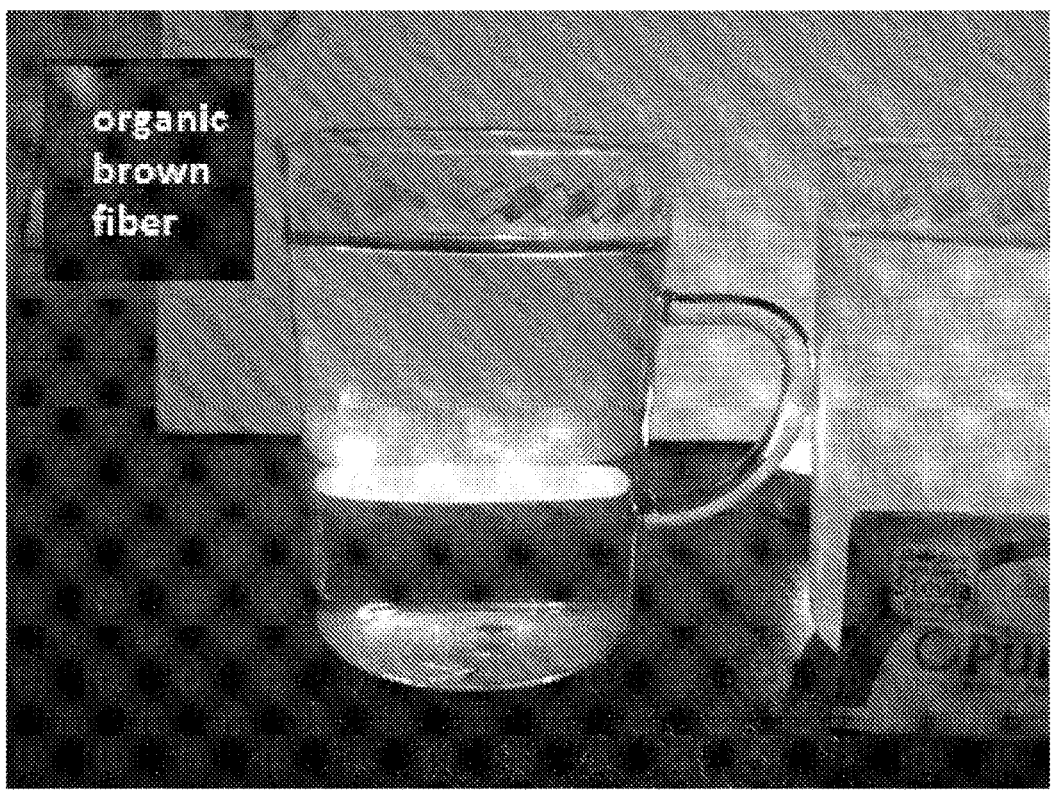
FIG. 3 provides a magnified image of the Left cup in FIG. 2 (composition comprising the "brown (organic) fiber").
Figure 4:
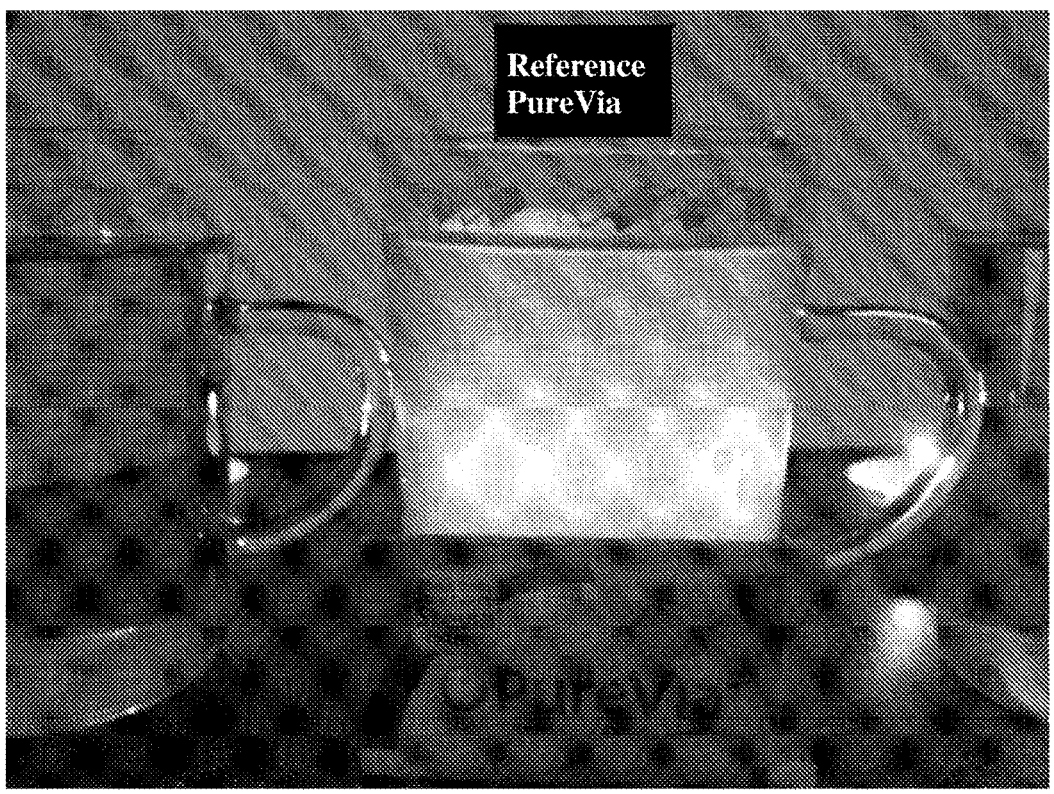
FIG. 4 provides a magnified image of the Center cup in FIG. 2 (PureVia).
Figure 5:
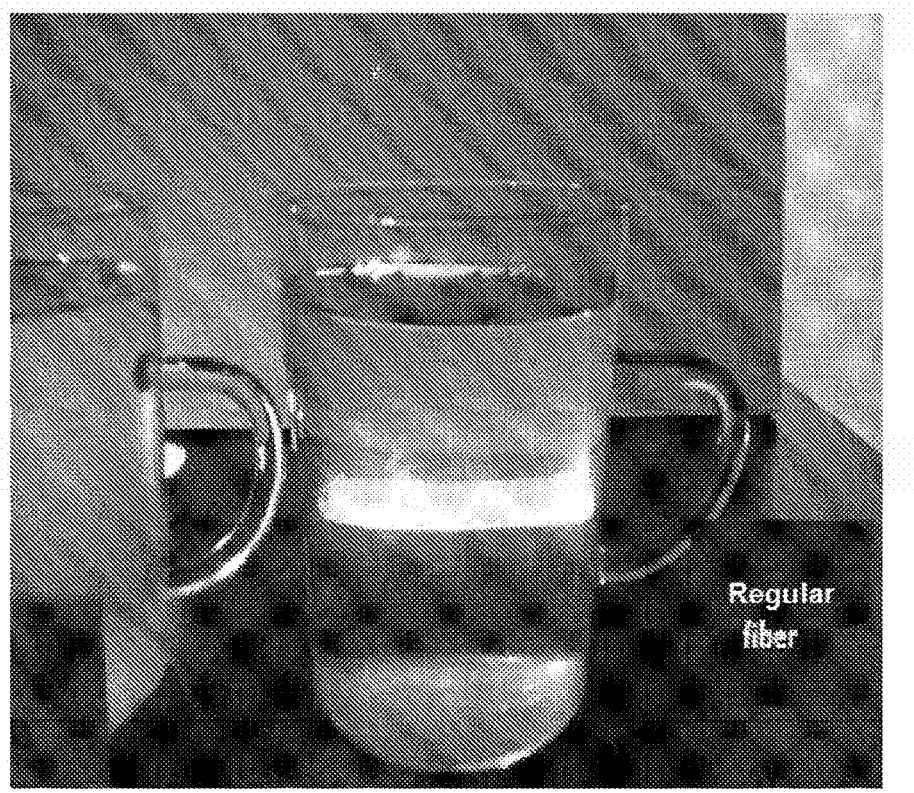
FIG. 5 provides a magnified image of the Right cup in FIG. 2 (composition comprising the "regular fiber").

The present disclosure is based on the finding that the combination (blend) of filler material comprising plant fibers, particularly *Acacia* fibers and *Stevia*, as a natural sucrose substitute, where the filler material constituted more than 90% of the total amount of the combination, resulted in a sweetening effect while being absent from the known unpleasant aftertaste typically ascribed to sweeteners comprising *Stevia*.

In addition, the present disclosure is based on the finding that when a composition according to the present disclosure was added to dairy product (milk or yogurt), the vanilla-like flavor of the dairy product (milk or yogurt) was enhanced.

All these findings were determined based on taste tests where an amount of a composition according to the present disclosure was mixed into either in an amount of water or milk and compared to the taste of water or milk in the absence of the composition or in comparison to the water/milk to which sugar or sugar substitute was added, all as described hereinbelow.

Additionally, it has been unexpectedly found that the combination is dissolved in water, leaving a clear solution after a couple of seconds of mixing 1 gr of a composition as disclosed herein in 180 ml water.

Yet further, it has been unexpectedly found that when a composition as disclosed herein is added to a citrus juice or to raw yogurt, the mixture maintained the pH of the juice or yogurt, and exhibited no phase separation or change in color.

Based on the findings which are further detailed below, it has been envisaged that the combination of water soluble plant fibers, such as *Acacia* fibers and a sucrose substitute of natural source, such as *Stevia*, can improve taste of various food products, or other orally delivered products (e.g. syrups).

Thus in its broadest aspect, the present disclosure provides a flavor modifying composition comprises a blend of
  (i) water soluble filler comprising plant fibers; and
  (ii) at least one sucrose substitute of natural source,
  wherein
    said flavor modifying composition comprises at least 90% w/w of the water soluble filler, the amount being determined when said composition is in dry form;
    said flavor modifying composition is water soluble.

In some embodiments, the at least one sucrose substitute of natural source has, in the absence of said filler, an unpleasant aftertaste that is masked in the flavor modifying composition, the masking being determined by a blind tasting test using a taste score between 1 to 5, 1 being most unpleasant aftertaste, where 1 gr of said flavor modifying composition is dissolved in 180 ml water at room temperature to obtain dissolved composition and the taste of the dissolved composition is compared by at least one individual to a reference taste score of a same amount of the sucrose substitute of natural source that is dissolved, in the absence of said filler, in 180 ml water at room temperature.

It has been found that when blended or dissolved into a food stuff, e.g. into coffee, the coffee was sweetened; or into milk, the vanilla-like flavor of the milk was enhanced as compared to the taste of the food stuff without the flavoring composition.

In the context of the present disclosure, "a flavor modifying composition" is to be understood as meaning a composition providing an individual with an improvement of at least one flavor sensation in the mouth (mouth feel). The improvement being determined by conventional blind taste tests as well known in the art (and also discussed below). In some embodiments, the improvement refers to an increase in one or more flavors.

Further, in the context of the present disclosure, the term "flavor" encompasses a sensory impression obtained with a composition subject of the present disclosure, when tasted alone or within a product to be given orally to a subject. The sensory impression includes, in accordance with some embodiments, a sweet sensed flavor or an improvement in an aroma of a product (e.g. vanilla aroma, caramel aroma). Accordingly, the flavor including aroma of food stuff can be altered with the composition disclosed herein.

When developing the flavor modifying composition disclosed herein, the inventor has aimed at providing a sensation that is, by commonly acceptable standards, immediate, intense and stable, and without any bad or bitter aftertaste impression as further discussed below. Without being bound by theory, the enhanced flavor effect obtained by the composition disclosed herein is believed to be associated with the combination of effects of the plant derived filler with the sucrose substitute of natural source (e.g., *Stevia*).

The flavor modifying composition comprises, at minimum, a filler material and a sucrose substitute of natural source as further defined herein.

In one specific aspect of the present disclosure, the flavor modifying composition is a sweetening composition and the blend/combination of the filler material and the sucrose substitute exhibit various improved sweetening properties as compared to these properties when the sucrose substituted was tasted in the absence of the filler material.

Thus, while the composition was found to particularly provide a sweetening effect, the present disclosure is not limited to this effect and the use of the composition for modifying (enhancement, reduction, masking etc) of other flavors is also applicable. For example, and as shown hereinbelow, the addition of the composition to milk provided the milk with an improved intense vanilla sensation that was not obtained in the milk in the absence of the composition.

Thus, in the following description, when referring to the composition disclosed herein and unless otherwise stated, it is to be understood to encompass the composition for modifying any flavor mutatis mutandis.

The "filler" in the context disclosed herein is the substance providing the bulk or majority of the composition and holds or carries other constituents. In some embodiments, the filler acts also to enhance the organoleptic and/or physical properties of the composition as discussed below. When referring to organoleptic properties, it is to be understood as the overall sensory impression upon consumption of food stuff and dissolution in the mouth, the organoleptic properties including, taste and texture.

Various fillers are known in the art and at times their selection relies on the amount of calorie-containing carbohydrates they contribute to the eventual composition. In this respect, and in the context with some embodiments of the present disclosure, the filler is selected from calorie-free or low-calorie filler substances, e.g., less than 2 kilocalories per gram (at times, also referred herein: "calories").

In some embodiments, the filler comprises fibers, preferably plant fibers. In yet some embodiments, the filler comprises dietary fibers, and at times, dietary plant fibers.

Generally, fibers may be soluble or insoluble in water. In the context of the present disclosure, the filler is water soluble and/or contains water soluble plant fibers, this being determined by the essentially complete dissolution, namely, essentially clear solution, when 1 gram of the filler or the composition comprising it as defined herein is mixed for 5 seconds with 180 ml water at room temperature. In some embodiments, the essentially complete dissolution is also observed at any temperature between 4° C. and room temperature, and further at times, at 4° C.

In some embodiments, the filler is soluble also in water containing dairy products, this being observed when the same dissolution test as described above is conducted with the dairy product used instead of the water. A dairy product in this context is a milk or milk substitute (soy, almond, rice and coconut milk) containing fluid product, preferably liquid, for example milk or any of soy, almond, rice and coconut milk.

Without being bound by theory, it appears that due to the high concentration of the filler in the composition as further discussed below, also the composition comprising it along with the at least one sucrose substitute is water soluble, i.e. essentially completely dissolves in water.

The essentially complete dissolution of the filler or the composition comprising it can be determined by visual inspection, where no particles or turbidity is viewed by a simple eye inspection. At times, an essentially complete dissolution can be determined spectroscopy, using UV-VIS spectrometer or other appliances commonly utilized for determined dissolution properties of substances (clarity), as known in the art. For example, the dissolution (clarity) can also be determined by UV spectrophotometry measurements and light absorbance at a wavelength of 490 nm, when 1 gr of the filler or the composition per se is dissolved in water, as described above. For determining clarity by any one of the above techniques, a solution of the composition can be prepared, for example, with 1 gr of the composition being mixed into 180 ml water for 5 seconds. The mixing can be at any temperature between about 4-6° C. to room temperature (25° C.). In some embodiments, the dissolution is evaluated at room temperature.

In some embodiments, the filler comprises plant fibers.

The term "plant fibers" is used herein to denote any fibrous containing material derived or obtained from a plant or plant part. The fibers may be comprised of a single type of substance, e.g. only polysaccharides, glycoproteins, proteins, and the like, or a combination of such substances. When referring to plant fibers (derived or obtained or extracted) material it is to be understood as encompassing any means of obtaining or separating the material from the plant, including, extraction. It should be understood that the term "fibers" is not limited to only the naturally obtained plant fibers, but can also encompass, in accordance with some embodiments, synthetic analogs of the naturally obtained substances. In some preferred embodiments, however, the fibers are of natural source, i.e. obtained directly from plants.

Plant fibers are included in the composition in an amount effective to provide the composition, in combination with the at least one sucrose substitute of natural source, with masking capability of any unpleasant aftertaste that is ascribed to the sucrose substitute with which it is blended. Namely, the sucrose substitute, in the absence of said fibers, has an unpleasant aftertaste in comparison to the aftertaste of the combination of the sucrose substitute with the fibers. This can be determined, without being limited thereto, in a blind tasting test where 1 gr of the composition is mixed into 180 ml water at room temperature and tasted by one or more individuals as compared to the taste of the sucrose substitute being similarly dissolved without said fibers. To quantitate the improvement in taste i.e. the masking of the unpleasant aftertaste, a taste score can be defined between 1 to 5, where 1 defines the most unpleasant aftertaste and the score of the composition is compared to the score obtained for the sucrose substitute alone (dissolved in water without the filler). At times, the blind tasting test can be conducted for a cold mixed composition at a temperature of 4° C. to 10° C., or even for a warm mixed composition at a temperature of 45° C. to 60° C. Generally, the blind test can be conducted at various temperatures of the samples, as long as the comparison is made in the same temperature.

Plant fibers include, without being limited thereto, *Acacia* fibers originating from the Fabaceae, Burseraceae, Ebenaceae, Tiliaceae, Poaceae, or any combination thereof. In accordance with some embodiments, the plant fibers are from Fabaceae, this includes, inter alia, *Acacia* gum (Arabic gum) fiber. In some other embodiments, the plant fibers are derived from Poaceae family species is corn fibers.

*Acacia* gum is a water soluble type of fibers that is obtained, for example, as exudates of hardened sap taken from mainly two species of the *Acacia* trees belonging to the Fabaceae family: *Acacia Senegal* and *Acacia Seyal*, although over a hundred of species of *Acacia* are known. *Acacia* gum is an edible biopolymer comprised of a complex mixture of carbohydrates (complex glycoproteins and polysaccharides by a high proportion of carbohydrates (~97%), which are predominantly composed of D-galactose backbone and side chains of D-glucuronic acid with terminal L-rhamnose or L-arabinose units and a low proportion of proteins (<3%)), having a low glycemic index and prebiotic effect (i.e., non-digestible fiber compounds that stimulate growth and/or activity of advantageous bacteria). The molecular weight of *Acacia* gum is between 200 and 600 kDa. *Acacia* gum is non-digestible in the human intestine and is used in the food industry as a stabilizer (E414). In some embodiments *Acacia* gum is obtained commercially.

In some embodiments the gum *Acacia* is obtained by processing crude exudates, the processing includes, without being limited thereto, drying (air drying, roller drying, spray drying) and mechanical milling (kibbing), to produce soluble granular material; and/or dissolving exudates in water under controlled (mild) heating conditions and stirring and removal of insoluble matter by decantation or filtering, optionally pasteurization and finally drying to produce the water soluble particulate fibers.

In some embodiments, the plant fibers are *Acacia* fibers derived from the *Acacia* tree species, e.g. from the *Acacia Seyal* tree and *Acacia Senegal* tree. Other types of species of *Acacia* trees useful for producing the plant fibers of the present disclosure include, without being limited thereto,

*Acacia Bussei, Acacia Drepanolobinn, Acacia Mellifera, Acacia Nilotica* and *Acacia Tortilis*.

*Acacia Senegal* and *Acacia Seyal* have some differences with respect to their chemical composition. They have the same sugar residues but *Acacia Seyal* gum has a lower content of rhamnose and glucuronic acid and higher content of arabinose and 4-O-methyl glucuronic acid than *Acacia Senegal*, yet *Acacia Seyal* gum contains a lower proportion of nitrogen and protein.

In some embodiments, the *Acacia* fibers are gum *Acacia* (also known as gum Arabic or as identified by the European food safety authority by the E number E414). Examples of *Acacia* fiber gums useful as the filler in the present invention are fiber gum B and fiber gum BioL in regular (white), organic form or brown (organic) form. In some embodiments, gum *Acacia* is derived or made of hardened sap taken from the *Acacia* tree (specifically from the *Acacia Seyal* tree and *Acacia Senegal* tree).

The composition can comprise gum *Acacia* as the sole filler material, yet in some embodiments, the gum *Acacia* is combined with other filler materials, including other fibers. A non-limiting list of fillers and fibers that can be combined with gum *Acacia* comprises fiber gum A, Actilight fiber (a short chain fructo-oligosaccharide) and corn fiber gum (a polysaccharide).

In some embodiments, gum *Acacia* can be defined by the dietary fiber content therein. *Acacia* fibers defined by their dietary fiber content include, without being limited thereto, fibers comprising less than 85% w/w dietary fiber content such as fiber gum A (also known as gum A); fibers comprising a dietary fiber content of more than 85% w/w, at times more than 90% w/w such as fiber gum B and fiber gum BioL (also known as gum BioL).

In some embodiments, the *Acacia* fibers comprise fiber gum B.

In some embodiments, the filler is essentially only *Acacia* (or gum *Acacia*), namely, there may be only trace amounts of other filler material such as other plant derived fibers that function or are known to be used as fillers.

The composition also comprises at least one sucrose substitute from natural source. When referring to a substance derived from natural source it is to be understood as one that is typically extracted from natural source by conventional extraction techniques. The natural source is typically a plant or plant part.

In some embodiments, the sucrose substitute is extracted from leaves of the plant species *Stevia Rebaudiana*. In some embodiments, the sucrose substitute is obtained by extraction of the leaves with hot water and the aqueous extract is then passed through an adsorption resin to trap and concentrate the component steviol glycosides which are the source of sweet taste. The resin is washed with a solvent alcohol to release the glycosides and product is recrystallized from methanol or aqueous ethanol. Ion exchange resins may be used in the purification process. The final product may be spray-dried.

In some embodiments, the sucrose substitute is or comprises *Stevia* (produced from the said leaves of the plant species *Stevia Rebaudiana*.

*Stevia* is enriched with sweet glycosides. Thus, in accordance with some embodiments, the composition comprises sweet glycosides. For example, the sweet glycosides of *Stevia* have steviol as the basic building block. Sweet glycosides include, without being limited, any one of the steviols selected from stevioside (known to be 250-300 more sweet than sugar), rebaudioside A (350-450× of sugar), rebaudioside C, dulcoside A, Rebaudioside B, Rebaudioside D, Rebaudioside E, steviobioside, and stevioglycoside.

In some embodiments, the *Stevia* sucrose substitute comprises one or combination of a member selected from the group consisting of stevioside, rebaudioside A, rebaudioside C, dulcoside A, Rebaudioside B, Rebaudioside D, Rebaudioside E steviobioside, and stevioglycoside.

In some further embodiments, the *Stevia* sucrose substitute comprises at least the combination of stevioside (13-[(2-O-β-D-glucopyranosyl-β-D-glucopyranosyl)oxy] kaur-16-en-18-oic acid, β-D-glucopyranosyl ester) and rebaudioside A (13-[(2-O-β-D-glucopyranosyl-3-O-β-Dglucopyranosyl-β-D-glucopyranosyl)oxy]kaur-16-en-18-oic acid, β-Dglucopyranosyl ester).

In some embodiments, the composition may include an additional (one or more) sucrose substitutes other than *Stevia*. For example, the composition can comprise sweet protein extracted from the fruit of *Katamfe*, namely, the low calorie protein *Thaumatin*.

In some embodiments, the composition is excluded of artificially produced sucrose substitutes or if artificial substitutes are present, they are in amount that cannot be regarded as contributing to the sweet taste of the resulting composition.

In some embodiments, the composition comprises a low calorie water soluble filler and at least *Stevia* as the sucrose substitute, the combination of same providing a low calorie product. When referring to a low-calorie composition it is to be understood as one providing less than 2 calories per 1 gram product, at times, providing less than 1.6 calories per 1 gram product, and further at times, less than 0.5 calories per 1 gram product, and yet further at times, 0 calories per 1 gram product. The reference to the amount of calories per 1 gram product of a sucrose substitute is governed by the regulation of food and dietary supplements by the U.S. Food and Drug Administration (FDA).

The amount of the filler in the composition is at least 90% when the composition is in dry form. In some embodiments, the amount of the filler in the total composition is at least 92% w/w, at times, any one of at least 95%, 96%, 97%, 98%, 99% each % constituting a separate embodiment.

In some embodiments, the composition comprises between 90% to 98% filler, at times, between 94% to 98% filler, at times, 96% to 98% filler, at times, 96% to 97% filler, at times, 96.5% to 97.5% filler, or even between 98% to 99.9% filler.

In some embodiments, the composition comprises between about 96% to 98% w/w of the filler and between about 2% to 4% w/w of the sucrose substitute of natural source. In some embodiments, the composition comprises between about 96% to 97% w/w of the filler and between about 3% to 4% w/w of the sucrose substitute of natural source.

The weight % in the compositions is determined when the composition is in dry form (i.e. not dissolved in any aqueous based media).

The amount of the sucrose substitute is very low as compared to that of the filler material. The amount of sucrose substitute in the composition is determined when in dry form (as discussed above). In some embodiments, the composition comprises a total weight of the sucrose substitute of between 0.02 to 0.1 gr per gram filler, at times, between 0.02 to 0.06 gr per gram filler, or between 0.03 to 0.05 gr per gram filler. In terms of ratio between the at least one sucrose substitute and filler material, and in accordance with some embodiments, the weight % ratio is between 1:10 and 1:50, at times, between 1:16 to 1:50, or even at times between 1:19 to 1:40, or even at times between 1:25 to 1:30.

When comprising sucrose substitutes other than *Stevia*, the additional substitute(s) can be in an amount ranging between 0.1 µg to 10 µg per gram filler. In some embodiments, the composition comprises as an additional sucrose substitute *Thaumatin* in an amount of between 0.1 µg to 10 µg per gram filler, at times, between 0.3 µg to 5 µg per gram filler, or alternatively between 0.4 µg to 2.1 µg per gram filler.

The composition can be provided and used in any solid dry form, including, without being limited thereto, fine powder, lyophilizate, granulate, tablets, etc.

In some embodiments, the composition is provided in liquid form, for example, as a solute in water (aqueous solution).

One characteristic of the composition disclosed herein is that it is physically and chemically stable upon exposure to a wide range of temperatures and pH. Specifically, no change or deterioration in any one of color, texture, firmness and/or odor of the solid dry composition and no phase separation of the liquid form of the composition were exhibited upon exposure to various temperatures between −5° C. and 180° C., at times, at temperature up to 50° C., at times, up to 100° C., at times, up to 150° C.; or to various pH levels between 3 to 8, at times, to pH levels between 4 to 8.

In some embodiments, the filler acts not only as a bulking agent but also as an anti-caking agent, i.e. exhibiting anti-caking properties on the overall components of the composition, thus, inherently contributing to the stability of the composition. A substance having anti-caking properties is one that prevents the formation of lumps, clumps or aggregates. This is of particular value when the dry composition is mixed with fluids, such as water and no aggregation takes place. Thus, the anti-caking property of the filler also assists in (i) dissolution; (ii) long storage of the composition in powder or liquid form.

The composition disclosed herein provides a change (increase or decrease or masking etc.) to a flavor of a product into which it is combined (e.g. mixed, blended), the product being of a kind that is orally. For simplicity, when referring herein to a oral product it is to be understood as any product that is to be introduced into an individual's mouth and consequently tasted by the individual.

In some embodiments, the oral product is a food/edible product. In one other embodiment the oral product is a hygienic oral care product. In yet another embodiment, the oral product is a pharmaceutical or a homeopathic product (e.g. in a form of a syrup).

The composition modifies a flavor in the oral product as compared to the flavor of the oral product in the absence of the composition. This is particularly beneficiary when the taste of the product is unpleasant (e.g. bitter, sour) or the oral product is poor in one or more desired tastes (e.g. sweetness, saltiness).

When referring to flavor modification it is to be understood as meaning either modifying a flavor that is also sensed in the product in the absence of the composition or reducing or masking of an unpleasant or otherwise undesired flavor in a product. For example, sweet or vanilla flavor enhancement of a flavor can be desired and yet bitterness masking can also be desired.

In some embodiments, the composition modifies an aftertaste in the product as compared to the aftertaste in the absence of the composition.

In some embodiments, the product has, in the absence of the composition an unpleasant aftertaste and when combined with an amount of the composition, the latter reduces the intensity of the unpleasant aftertaste. The improvement in flavor (such as a reduced unpleasant aftertaste) can be determined by a blind tasting test where 1 gr of said the composition is introduced into a fixed amount of the product and the thus modified product is tasted (blind tasting) in comparison with the product without the said composition.

In one example, the product is milk. When 1 gr of the composition was mixed into said 180 ml milk, an intensified creamy milky vanilla sensation (flavor) was felt for the milk supplemented with the composition in comparison to the pristine cup of milk (without the composition). Generally, for reproducibility of a blind test, the comparison is to be conducted on the same amount of product (i.e. with or without the composition), under the same mixing time and temperature. Further, the blind test can be conducted at various temperatures of the samples, as long as the comparison is made in the same temperature.

In some embodiments, the modification in flavor can also be compared to commercially available flavor modifying agents. For example, a sweetening effect of the composition was compared to products comprising other sucrose substitutes, such as Splenda or Pure Via (commercial package (1 gr)) and it was found that the other sucrose substitute are inferior in flavor (sweet) enhancement.

The modification of flavor by the composition disclosed herein can be characterized by any one of the following parameters, the characteristic being defined by a scoring system having a score scale from 1 to 5, with 1 being the most inferior flavor property.

flavor immediacy—denoting the time (typically in seconds) by which the flavor is sensed after being introduced into the individual's mouth. Accordingly, when flavor is senses only after more than 5 seconds, the score of the flavor immediacy is scored 1; and when the flavor is sensed in the first second, the flavor immediacy is scored 5.

The composition of the present disclosure was found to either maintain or increase, by at least one level (score) immediacy of at least one desired flavor of a product. This is exemplified below with respect to sweetness flavor.

flavor intensity—denoting the intensity of the flavor sensed with a weak flavor being scored 1 and a strong flavor being scored 5.

The composition of the present disclosure was found to either maintain or increase, by at least one level (score) intensity of at least one desired flavor of a product. This is exemplified below with respect to sweetness flavor.

flavor stability—denoting the duration of sensing a flavor, i.e. time lasting of the flavor taste after being introduced into the mouth, where when a flavor is sensed only in a first second is scored 1, and a flavor that lasts more than 5 seconds is scored 5.

flavor profile: defined by an average score level of flavor immediacy, sweetness intensity and sweetness stability The composition of the present disclosure was found to either maintain or increase, by at least one level (score) stability of at least one desired flavor of a product. This is exemplified below with respect to sweetness flavor.

temperature stability—denoting no sensed change in score of at least flavor intensity after exposure of the product to a temperature above room temperature, at times, up to 50° C., at times up to 100° C., or even up to 150° C.;

pH stability—denoting no sensed change in score of at least flavor intensity or physical deterioration of a product comprising the composition (e.g. color change, phase separation etc) after exposure of the product to any pH from 3 to 8, at times, at a pH of between 4 to 8;

Temperature stability—denoting no sensed change in score of at least flavor intensity or physical deterioration of a product comprising the composition (e.g. color change, phase separation etc) after exposure of the product to any temperature up to 150° C., at times, to any temperature between 4° C. to 150°, or to 100°.

Further, a composition according to the present disclosure was also found to be temperature and/or pH stable when exposed to temperature of 45° C. continuously for 20 hours at pH of 4 and no phase separation and color change were observed.

A composition according to the present disclosure was also found to be both temperature and/or pH stable when exposed to temperature of 37° C. continuously for three months at pH of 3.3 to 4.5. In addition, when mixed into citrus juice no.
  bitter, licorice or acidic aftertaste—denoting the existence of an aftertaste (side-taste), typically undesired with respect to the product, where an intense aftertaste is scored 1, and no side taste is scored as 5.

The composition of the present disclosure was also found to mask bitter aftertaste of the sucrose substitute as noted above.

In one preferred embodiment, the flavor modifying composition is a sweetening composition. A "sweetening composition" is a composition to be consumed by animal, in particular human individuals and to provide the individual with at least a sweet sensation in the mouth. When developing the composition as a sweetening composition, the inventor has aimed at providing a sweet sensation that is immediate, intense and stable, and without any bad or bitter taste as further discussed below.

The art of sweeteners makes use of various fillers most of which are calorie-containing carbohydrates such as dextrose and maltodextrin (ten grams of these fillers provide about 35 kilocalories compared to 39 kilocalories for sugar). The sweetening composition disclosed herein has less than 2 kilocalories as described hereinabove.

The sweetening composition disclosed herein can be characterized by any of the above listed properties. The scoring for the sweetening composition was compared to sucrose as a reference, the results of which are provided in the table below:

| Property | Sucrose | Sweetening Comp. [average] |
|---|---|---|
| | | Score (1-5) |
| Sweetness Immediacy | 3 | 3-5 [4] |
| Sweetness Intensity | 3 | 3-5 [4] |
| Sweetness Stability | 3 | 3-5 [4] |
| bitter, licorice or acidic taste | 3 | 1-2 [1.5] |

The composition may have various applications. This include, without being limited thereto (each of the following constituting a separate embodiment of the present disclosure), as a supplement in the food and beverages industry, in the dairy industry, i.e., dairy products, yoghurts and puddings, in the pharmaceutical industry, in the naturopathic industry, nutraceutical industry and other healthcare products (e.g. toothpaste, mouthwash); candy and gum industry, or any other application that requires the use of a flavor modifying composition as an excipient or additive. As such, the present disclosure also provides the use of the composition as defined herein for the preparation of a product designed to come in contact with a subject's taste buds.

In some embodiments, the composition is for use as a sweetener in products that necessitate or involve contact of the product with the taste buds.

Finally, the present disclosure provides products that are required or involve contact with taste buds, the product comprising the composition disclosed herein.

SOME NON-LIMITING EXAMPLES

Example 1

Composition Preparation and Characterization

Composition Preparation
Materials:
  For preparing the flavor modifying composition the following ingredients were used:

TABLE 1

Ingredients used in preparation of the flavor modifying composition

| Ingredient | Manufacturer |
|---|---|
| Regular (white) *Acacia* Fiber | Nexira, *Acacia* Seyal gum, 90% dietary fibers |
| Brown (organic) *Acacia* Fiber | Nexira, organic *Acacia* Seyal gum BioL, 90% dietary fibers |
| *Stevia* | *Stevia* comprising at least about 95% rebaudioside A (Purecircle) |

Method:
  The flavor modifying composition comprising the ingredients specified in Table 1 was prepared by mixing 1 gram of the filler (comprising one of regular or brown *acacia* fiber) with a desired amount of *Stevia* (96:4% w/w, fiber: *Stevia* ratio), as indicated in the following Methods and Results *Stevia* comprising at least about 95% rebaudioside A. Then, for the preparation of a solution, 1 gram of the filler-*Stevia* blend was added to 180 ml water, at room temperature, without mixing (FIG. 1) or with mixing (by magnetic stirring, FIGS. 2-5).

In the following description, when using a regular *Acacia* fiber the term "regular composition" or "regular fiber" is used. When using an organic brown fiber, the composition is termed "brown composition" or "brown fiber" is used.

Composition Characterization
Materials:
  For the comparison, the commercial products Splenda® and Pure Via® were used:
Methods:
  The sweetness profile of the regular composition was compared with a tea spoon amount of sugar and with the commercial dose corresponding to a tea spoon of sugar of two sugar substitutes, Splenda® and Pure Via®. Liquid samples were prepared by mixing in a cup the amount of the composition or the commercial sugar substitute in water and after 5 seconds of mixing, determining for each cup one or more of the following flavor-related parameters (all being defined hereinabove):
  Clarity (visually determined), transparency (determined using conventional spectroscopy techniques) of liquid composition; flavor (e.g. sweetness and/or aroma) immediacy; flavor (e.g. sweetness and/or aroma) intensity; flavor (e.g. sweetness and/or aroma) profile; flavor (e.g. sweetness and/or aroma) stability; aftertaste (e.g. licorice, bitter and/or acidic taste).

In addition, glycemic blood values were determined from blood glucose level of a blood sample taken from a patient 30 minutes after consuming 5 gram of the composition in 180 ml water.

Also, in addition the general taste feeling, namely, the subjective observation of the individual, was considered.

Results

The clarity of the composition comprising vis-à-vis the commercial product PureViva® is presented in FIGS. 1 to 5.

FIGS. 1 to 5 provide images of liquid forms of a composition disclosed herein dissolved in water, vs. the commercially available products PureVia. As shown, even without stirring, the solution containing the composition of the present disclosure including regular fibers and the solution containing the composition of the present disclosure with brown (organic) fibers were clear and transparent (at 4° C.). However, at the same temperature, with the same amount of commercial PureVia, and even after stirring for 5 seconds (FIG. 2) the cup containing PureVia in water (at 4° C.) was opaque (middle cup).

Table 1A below summarizes sweetening properties of the composition according to some embodiments,

TABLE 1A

Properties of the regular composition (96:4% w/w, fibers:*Stevia* ratio)

| Property | Determined level |
|---|---|
| Clarity | Visually clear |
| Transparency (determined by spectroscopy) | 92% |
| Licorice taste | 1 |
| Bitter taste | 1.2 |
| Acidic taste | 1 |
| Lasting taste | 2.2 seconds |
| Sugar-like feeling | 4.3 |
| Glycemic blood value changes | Less than 100 mg/dl |

Table 1B shows parameters comparison between a composition containing regular fiber and two commercial products tested with respect to the various tested taste parameters.

TABLE 1B

Comparison of the regular composition with sugar, Splenda and Pure Via (96:4% w/w, fiber:*Stevia* ratio)

| Tested comparison | Composition Score | Reference Score |
|---|---|---|
| Sweetness immediacy vs. sugar | 3 | 3 |
| Sweetness immediacy vs. Splenda | 3 | 2 |
| Sweetness immediacy vs. Pure Via | 5 | 1.8 |
| Sweetness intensity vs. sugar | 3 | 3 |
| Sweetness intensity vs. Splenda | 4 | 4 |
| Sweetness intensity vs. Pure Via | 5 | 2 |
| Sweetness stability vs. sugar | 3 | 3 |
| Sweetness stability vs. Splenda | 3 | 4 |
| Sweetness stability vs. Pure Via | 5 | 2 |

Specifically, in Table 1A, the clarity of the regular composition at room temperature was evaluated and was found to be very high (essentially totally clear). In addition, the transparency of the examined regular composition at room temperature was evaluated to be 92%, (measured spectroscopically). The results indicate the high solubility of the composition.

Table 1B shows a comparison of the organoleptic properties of the exemplary regular composition with sugar, Splenda and Pure Via. The regular composition was prepared similarly to the composition described in Example 1 (1 gr of regular composition comprising 96:4% w/w fibers: *Stevia* ratio mixed in 180 ml water).

The flavor (in this case sweetness) immediacy, intensity and stability values for the regular composition was similar to that of sugar, and exhibited a more profound sweetness immediacy, intensity and stability than Splenda/PureVia.

In addition, the regular composition did not leave any licorice or acidic aftertaste, nor a bitter taste after consumption and the volunteers also indicated the experience of a substantially natural feeling with the composition of the invention.

In an additional experiment, when the regular composition was mixed in 180 ml milk, the volunteers mentioned a milky, strong vanilla after taste.

In conclusion, the compositions disclosed herein, irrespective of whether the fiber is regular, organic or brown, provide a sugar substitute that provides a clear solution (highly water-miscible), with high resemblance in taste and feeling to that obtained with sugar and improved properties with respect to commercially tested artificial products.

Example 2

Determining Best Fiber and *Stevia* Content

The taste properties of different concentrations of *Stevia* in the compositions of *Stevia* and different types of plant fibers were compared with the feeling sensed with sucrose as the reference sample (tea spoon amount of sucrose dissolved in 180 ml water).

Materials:

Specifically, the following fibers were combined with *Stevia* and tested: *Stevia* comprising at least about 95% rebaudioside A.

Actilight fiber (950P) from Beghin Meiji comprising a mixture of fructo-oligosaccharides (FOS) which are soluble dietary fibers.

Fiber gum A and Fiber gum B (*acacia* fiber) from Nexira, *Acacia Seyal* gum.

*Stevia* was combined with each of the above fillers at different concentrations in 1 gram filler to obtain final *Stevia* concentrations ranging from 0.01 to 0.1 gram per 1 gram filler as indicated in each of the following Tables 2A-2I. Each specific combination in Tables 2A-2I was mixed into water at a concentration of 1 gr composition in 180 ml water. Some compositions included a combination of fiber gum A and fiber gum B (50:50% w/w ratio, 30:70 or 70:30) with *Stevia*.

Some other samples were prepared by combining the filler material typically comprised in commercial sweeteners such as erythritol known as the filler in PureVia® and dextrose known as the filler in Splenda® (as well as a calorie-containing carbohydrate masking agent in Splenda®) with *Stevia* at various *Stevia* concentrations (Tables 2A-2B).

As noted above, for the taste evaluation by individuals, the different filler-*Stevia* compositions were mixed by dissolution of 1 gr of each of the specified composition in 180 ml water or a tea spoon (5 gr) of sucrose in 180 ml water.

The sweetness (defined as weak (score of 1-2), same (score of 3) or strong (score of 4-5)) and taste (bitter, licorice or acidic) of each composition was evaluated by 4 individuals in comparison with the taste of the sucrose sample. The results are displayed for each of the compositions in Tables 2A-2I.

TABLE 2A

Stevia combined with erythritol

| Stevia (gr Stevia per 1 gr erythritol) | Weak | Same | Strong | Bitter | Licorice | Acidic |
|---|---|---|---|---|---|---|
| 0.01 | ✓ | | | ✓ | | |
| 0.02 | ✓ | | | ✓ | | |
| 0.03 | ✓ | | | ✓ | ✓ | ✓ |
| 0.04 | ✓ | | | ✓ | ✓ | ✓ |
| 0.05 | ✓ | | | ✓ | ✓ | ✓ |
| 0.06 | ✓ | ✓ | | ✓ | ✓ | ✓ |
| 0.07 | | ✓ | ✓ | ✓ | ✓ | ✓ |
| 0.08 | | ✓ | ✓ | ✓ | ✓ | ✓ |
| 0.09 | | | ✓ | | ✓ | ✓ |
| 0.1 | | | ✓ | | ✓ | ✓ |

Table 2A shows that compositions comprising erythritol as the filler (carrier for *Stevia*), irrespective of the *Stevia* concentration, had negative taste impressions, i.e., bitter, licorice and/or acidity.

TABLE 2B

Stevia combined with dextrose

| Stevia (gr Stevia per 1 gr dextrose) | Weak | Same | Strong | Bitter | Licorice | Acidic |
|---|---|---|---|---|---|---|
| 0.01 | ✓ | | | | | |
| 0.02 | ✓ | | | | | |
| 0.03 | ✓ | ✓ | | | | |
| 0.04 | ✓ | ✓ | | | | |
| 0.05 | | ✓ | ✓ | | | |
| 0.06 | | ✓ | ✓ | | ✓ | ✓ |
| 0.07 | | | ✓ | | ✓ | ✓ |
| 0.08 | | | ✓ | | ✓ | ✓ |
| 0.09 | | | ✓ | | ✓ | ✓ |
| 0.1 | | | ✓ | | ✓ | ✓ |

Table 2B shows that at a concentration of 0.01-0.04 gr *Stevia* per 1 gr dextrose, only a weak sweet taste is obtained as compared to the taste of sucrose. However, at the same time, the compositions with the different *Stevia* concentrations had no negative taste impressions (bitter, licorice and/or acidic). At 0.05 gr *Stevia*, the taste was similar to sucrose. While increasing the level of *Stevia* increased also the sweetness of the composition, a licorice and acidic taste was experienced.

TABLE 2C

Stevia with actilight fiber composition

| Stevia | Weak | Same | Strong | Bitter | Licorice | Acidic |
|---|---|---|---|---|---|---|
| 0.01 | ✓ | | | | | |
| 0.02 | ✓ | | | | | |
| 0.03 | | ✓ | | | | |
| 0.04 | | ✓ | | ✓ | ✓ | ✓ |
| 0.05 | | ✓ | | ✓ | ✓ | ✓ |
| 0.06 | | | ✓ | ✓ | ✓ | ✓ |
| 0.07 | | | ✓ | ✓ | ✓ | ✓ |
| 0.08 | | | ✓ | ✓ | ✓ | ✓ |
| 0.09 | | | ✓ | ✓ | ✓ | ✓ |
| 0.1 | | | ✓ | ✓ | ✓ | ✓ |

Table 2C above shows that at *Stevia* concentrations above 0.03 gr per 1 gram actilight fiber the sweetness taste is similar to that of sucrose. Also, the tested individuals indicated that no bad after taste was felt.

TABLE 2D

Stevia combined with fiber gum A

| Stevia | Weak | Same | Strong | Bitter | Licorice | Acidic |
|---|---|---|---|---|---|---|
| 0.01 | ✓ | | | | | |
| 0.02 | ✓ | | | | | |
| 0.03 | ✓ | | | ✓ | ✓ | ✓ |
| 0.04 | ✓ | | | ✓ | ✓ | ✓ |
| 0.05 | ✓ | | | ✓ | ✓ | ✓ |
| 0.06 | | ✓ | ✓ | ✓ | ✓ | ✓ |
| 0.07 | | ✓ | ✓ | ✓ | ✓ | |
| 0.08 | | | | ✓ | ✓ | ✓ |
| 0.09 | | | | ✓ | ✓ | ✓ |
| 0.1 | | | | ✓ | ✓ | |

Table 2D shows that the composition with fiber gum A was as sweet as sucrose at *Stevia* concentrations above 0.06 gr per 1 gram fiber. However, the compositions with fiber gum A compositions were found to be bitter and licorice and with some also having acidic feeling ad *Stevia* concentrations above 0.02 gr per 1 gram fiber.

TABLE 2E

Stevia combined with fiber gum B

| Stevia | Weak | Same | Strong | Bitter | Licorice | Acidic |
|---|---|---|---|---|---|---|
| 0.01 | ✓ | | | | | |
| 0.02 | ✓ | | | | | |
| 0.03 | | ✓ | | | | |
| 0.04 | | ✓ | | | | |
| 0.05 | | ✓ | ✓ | | | |
| 0.06 | | | ✓ | ✓ | ✓ | |
| 0.07 | | | ✓ | ✓ | ✓ | |
| 0.08 | | | ✓ | ✓ | ✓ | ✓ |
| 0.09 | | | ✓ | ✓ | ✓ | ✓ |
| 0.1 | | | ✓ | ✓ | ✓ | ✓ |

Table 2E shows that the combination of *Stevia* and fiber gum B at concentrations 0.03 gr, 0.04 gr and 0.05 gr (corresponding to w/w concentrations of between 94% and below 98% out of the total concentration of the fiber), provided a sweet taste (same or even stronger than sucrose) and without any bitterness, acidic or licorice sensations.

Taking these results together with the clarity of the solution comprising these ingredients, led to further investigate combinations comprising at least *Stevia* with fiber gum B. Specifically, various ratios between fiber gum B, with fiber gum A were tested, including a fiber gum A:fiber gum B w/w ratio of 50:50, 30:70 or 70:30; the results of which are presented in Tables 2F, 2G and 2H respectively.

TABLE 2F

Stevia combined with fiber gum A:fiber gum B 50:50

| Stevia | Weak | Same | Strong | Bitter | Licorice | Acidic |
|---|---|---|---|---|---|---|
| 0.01 | ✓ | | | | ✓ | ✓ |
| 0.02 | ✓ | | | | ✓ | ✓ |
| 0.03 | ✓ | ✓ | | | ✓ | ✓ |
| 0.04 | ✓ | ✓ | | | ✓ | ✓ |
| 0.05 | | ✓ | ✓ | ✓ | ✓ | ✓ |
| 0.06 | | | ✓ | ✓ | ✓ | ✓ |
| 0.07 | | | ✓ | ✓ | ✓ | |
| 0.08 | | | ✓ | ✓ | ✓ | |
| 0.09 | | | | ✓ | ✓ | |
| 0.1 | | | | ✓ | ✓ | |

TABLE 2G

Stevia combined with fiber gum A:fiber gum B 30:70

| Stevia | Weak | Same | Strong | Bitter | Licorice | Acidic |
|---|---|---|---|---|---|---|
| 0.01 | ✓ | | | | | |
| 0.02 | ✓ | | | | | ✓ |
| 0.03 | ✓ | | | | | ✓ |
| 0.04 | ✓ | | | ✓ | ✓ | ✓ |
| 0.05 | ✓ | | | ✓ | ✓ | ✓ |
| 0.06 | | ✓ | ✓ | ✓ | ✓ | ✓ |
| 0.07 | | | ✓ | ✓ | ✓ | |
| 0.08 | | | ✓ | ✓ | ✓ | |
| 0.09 | | | ✓ | ✓ | ✓ | |
| 0.1 | | | ✓ | ✓ | | |

TABLE 2H

Stevia combined with fiber gum A:fiber gum B 70:30

| Stevia | Weak | Same | Strong | Bitter | Licorice | Acidic |
|---|---|---|---|---|---|---|
| 0.01 | ✓ | | | | | |
| 0.02 | ✓ | | | | | |
| 0.03 | ✓ | | | | | |
| 0.04 | ✓ | | | | | ✓ |
| 0.05 | ✓ | ✓ | | ✓ | ✓ | ✓ |
| 0.06 | | ✓ | ✓ | ✓ | ✓ | ✓ |
| 0.07 | | | ✓ | ✓ | ✓ | ✓ |
| 0.08 | | | ✓ | ✓ | ✓ | |
| 0.09 | | | ✓ | ✓ | ✓ | |
| 0.1 | | | ✓ | ✓ | ✓ | |

The combinations above suggest that fiber gum B is the best choice of a main fiber (at least 50% from the total amount of water soluble fibers), at least in terms of flavor enhancement, clarity and stability of the taste.

Example 3

Composition Comprising *Acacia* Fiber and *Stevia* in Dairy Products

The flavor change of the composition comprising *Stevia* and *Acacia* fiber was evaluated when added into two dairy products: 1) 180 ml milk (3% fat) and 2) 150 ml unsweetened yogurt (3-4.5% fat).

*Stevia* was combined with *Acacia* fiber at different concentrations to obtain different compositions. Then 1 gram of each of the compositions was added into each one of 180 ml milk sample or 150 ml yogurt sample as indicated in Table 3, and stirred for 5 seconds. Some compositions included a combination of *Acacia* fibers with *Stevia* at an effective amount according to the present disclosure (96:4% w/w or 97:3% w/w, total fiber:*Stevia* ratio).

Comparison of Effect with Commercial Products
Materials:
For comparison, the commercial products: Splenda®, Pure Via® and sucrose (table sugar) were added to the same dairy products above.
Methods:
The flavoring impact of two *Acacia* fiber gum B/*Stevia* compositions (96:4% w/w or 97:3% w/w, fiber:*Stevia* ratio) disclosed herein was compared with one (5 gram) and two (10 gram) tea spoon amounts of sugar or 1 gram of a commercial products (Splenda® and PureVia®), this amount corresponding to 1 tea spoon sugar as indicated in Table 3.
Samples for tasting were prepared by mixing the above-mentioned indicated amounts for the compositions disclosed herein or the corresponding fixed amount for the commercial products in 180 ml milk sample or 150 ml yogurt sample and analyzed as follows:

The change in the vanilla-creamy feeling (flavor/aroma) was scored in a scale of 1-5, where '1' indicated a weak vanilla-creamy flavor and '5' indicated a strong vanilla-creamy flavor. The average from results of 25 volunteers was compared with the taste of the commercial samples. All samples were at 4-10° C. The results are displayed for each of the combinations in Table 3.

TABLE 3

Comparison of Vanila aroma in dairy products

| Composition/ commercial product | Amount of sample in product | Milk | Yogurt |
|---|---|---|---|
| Sugar | 1 tea spoon (5 gr) | 2.4 | 2.0 |
| Sugar | 2 tea spoons (10 gr) | 2.7 | 2.4 |
| Splenda ® | 1 gr | 1.9 | 1.9 |
| Pure Via ® | 1 gr | 1.2 | 1.0 |
| Acacia fiber:*Stevia* (96:4% w/w) | 1 gr | 3.5 | 3.1 |
| Acacia fiber:*Stevia* (97:3% w/w) | 1 gr | 3.8 | 3.5 |

Results

Table 3 shows that when sugar was added to the milk or yogurt samples, the samples had a slight creamy vanilla milky flavor, ranking at an average score of 2.4 and 2.0 respectively. Incorporation of an additional tea spoon of sugar enhanced the creamy vanilla milky flavor (average score of 2.7 or 2.4 for milk and yogurt samples, respectively).

Table 3 further shows that PureVia added to milk or yogurt, exhibited a score of 1.2 and 1.0, respectively, with respect to the creamy milky flavor experienced for the dairy samples tasting tests. Namely, had a weak creamy vanilla milky flavor, i.e. the commercial substitutes did not enhance the milky flavor of the dairy samples.

Further, Table 3 shows that Splenda added to milk or yogurt, exhibited a slightly more enhanced creamy vanilla milky flavor as compared to PureVia, ranking at an average score of 1.9 for both dairy products.

An increase in intensity of the creamy milky vanilla flavor was obtained for the dairy products to which the composition according to an embodiment of the present invention was exhibited with a score of 3.5 and 3.1 respectively, as shown in Table 3.

Yet even more profound creamy milky vanilla flavor was obtained for the composition comprising 97:3% w/w *Acacia*:*Stevia* in milk and yogurt, respectively (score of 3.8 and 3.5, respectively).

Additionally, the two tested *Acacia*:*Stevia* compositions did not leave any bitter, licorice or acidic taste impression and the volunteers also indicated the experience of a substantially natural feeling (creamy milky, strong vanilla flavor).

Example 4

Stability of a Composition Comprising *Acacia* Fiber and *Stevia* (96:4% w/w *Acacia*:*Stevia*)

Example 4A

Stability in Citrus Juice

The stability of the sweet flavor of citrus juice into which the *Acacia*:*Stevia* composition was added was evaluated.

Notably, citrus juice typically has a pH of 3.3-4.19. The juice comprising the *Acacia* fiber:*Stevia* composition was maintained at 37° C. for three months.

The initial and final pH of the juice with *Acacia* fiber:*Stevia* was measured during this period and was found to be pH stable with no phase separation in the juice.

Example 4B

Stability in Raw Yogurt

The pH stability of raw yogurt (i.e., unsweetened yogurt starter, identifier: "JOG331A Medium") into which *Acacia*:*Stevia* composition was added was evaluated herein and compared to the stability of same yogurt into which an sweetening equivalent amount of sucrose was added. As reference, the raw yogurt was used. Each sample was maintained at 45° C. for 20 hours.

The measured pH levels of the raw yogurt as is (reference), or with sucrose (5% w/w sucrose in sample) or with *Acacia*:*Stevia* composition (0.55 w/w % composition in sample) are shown in Table 1, from left to right respectively.

The pH of the different samples was measured by a pH meter every 30 minutes. It was found that the pH values of the raw yogurt (reference), the raw yogurt comprising sucrose and the raw yogurt comprising the *Stevia*:*Acacia* composition were essentially unchanged during the measurements.

TABLE 5 pH values of raw yogurt with and without sweetening composition

| Time (h) | Raw Yogurt | Raw Yogurt + Sucrose (5% w/w) | Raw Yogurt + Fiber:*Stevia* (96:4) composition (0.55 w/w %) |
|---|---|---|---|
| 0 | 6.6 | 6.6 | 6.59 |
| 0.5 | 6.58 | 6.59 | 6.57 |
| 1 | 6.53 | 6.54 | 6.52 |
| 1.5 | 6.38 | 6.41 | 6.35 |
| 2 | 5.89 | 6.01 | 5.96 |
| 2.5 | 5.48 | 5.5 | 5.46 |
| 3 | 5.05 | 5.08 | 5.04 |
| 3.5 | 4.89 | 4.9 | 4.88 |
| 4 | 4.79 | 4.77 | 4.78 |
| 4.5 | 4.68 | 4.67 | 4.7 |
| 5 | 4.62 | 4.6 | 4.65 |
| 5.5 | 4.56 | 4.54 | 4.6 |
| 6 | 4.52 | 4.5 | 4.56 |
| 6.5 | 4.49 | 4.47 | 4.52 |
| 7 | 4.46 | 4.44 | 4.48 |
| 7.5 | 4.44 | 4.41 | 4.45 |
| 8 | 4.42 | 4.39 | 4.42 |
| 8.5 | 4.39 | 4.37 | 4.39 |
| 9 | 4.37 | 4.35 | 4.37 |
| 9.5 | 4.34 | 4.33 | 4.34 |
| 10 | 4.32 | 4.32 | 4.32 |
| 10.5 | 4.3 | 4.31 | 4.3 |
| 11 | 4.28 | 4.3 | 4.28 |
| 11.5 | 4.27 | 4.29 | 4.27 |
| 12 | 4.25 | 4.28 | 4.25 |
| 12.5 | 4.24 | 4.27 | 4.24 |
| 13 | 4.23 | 4.26 | 4.23 |
| 13.5 | 4.22 | 4.25 | 4.22 |
| 14 | 4.21 | 4.25 | 4.21 |
| 14.5 | 4.2 | 4.24 | 4.2 |
| 15 | 4.19 | 4.24 | 4.19 |
| 15.5 | 4.18 | 4.23 | 4.18 |
| 16 | 4.18 | 4.23 | 4.18 |
| 16.5 | 4.17 | 4.22 | 4.17 |
| 17 | 4.17 | 4.22 | 4.17 |
| 17.5 | 4.16 | 4.22 | 4.16 |
| 18 | 4.16 | 4.21 | 4.16 |
| 18.5 | 4.16 | 4.21 | 4.16 |
| 19 | 4.16 | 4.21 | 4.16 |
| 19.5 | 4.15 | 4.21 | 4.15 |
| 20 | 4.15 | 4.21 | 4.15 |

The invention claimed is:

1. A water soluble composition, comprising:
   a water soluble filler comprising *acacia* plant fibers; and
   a natural sucrose substitute comprising an extract of *Stevia Rebaudiana*, the extract of *Stevia Rebaudiana* comprising at least about 95% rebaudioside A,
   wherein said *acacia* plant fibers are present in an amount of between about 94% to about 98% w/w based on total weight of said composition as determined when said composition is in dry form,
   wherein the *acacia* plant fibers comprise fiber gum having a dietary fiber content of at least 85% w/w, and
   wherein, when the composition is in dry form, the natural sucrose substitute is present in an amount of from 0.03 gr to 0.05 gr per 1 gr of fiber gum.

2. The composition of claim 1, wherein said extract of *Stevia Rebaudiana* is present in an amount of between about 2% to about 4% w/w based on total weight of said composition as determined when said composition is in dry form.

3. The composition of claim 1, wherein the filler further comprises an additional fiber selected from the group consisting of fiber gum A, a short chain fructo-oligosaccharide and corn fiber gum.

4. The composition of claim 1, wherein the filler further comprises one or more plant fiber obtained from a plant family selected from the group consisting of Burseraceae, Ebenaceae, Tiliaceae and Poaceae, or a combination thereof.

5. The composition of claim 1, wherein the extract of *Stevia Rebaudiana* comprises one or more *stevia* component selected from the group consisting of stevioside, rebaudioside C, dulcoside A, rebaudioside B, rebaudioside D, rebaudioside E, steviobioside, and stevioglycoside.

6. The composition of claim 5, wherein the extract of *Stevia Rebaudiana* comprises stevioside and rebaudioside A.

7. The composition of claim 1, further comprising one or more additional natural sucrose substitutes.

8. The composition of claim 1, wherein the one or more additional natural sucrose substitute is Thaumatin.

9. The composition of claim 1, wherein one gram of the composition has a calorie content of less than 2 calories.

10. The composition of claim 1, wherein the composition does not comprise any artificially produced sucrose substitutes.

11. The composition according to claim 1, wherein when administered to a patient a change in glycemic blood value of less than 100 mg/dl occurs when measured about 30 minutes after administration.

12. A solution, comprising the composition of claim 1 and water, wherein at least 90% of the composition is dissolved when about 1 gram of the composition is mixed with about 180 ml of water for about 5 seconds at room temperature.

13. A pharmaceutical or food product, comprising: the composition according to claim 1.

14. The product of claim 13, selected from the group consisting of an oral care product, food product, food-supplement product or drug product.

15. A method of sweetening an oral product, comprising: adding the composition of claim 1 to said oral product in an amount sufficient to provide a sweetening effect on said oral product to produce a sweetened oral product.

16. The method of claim 15, wherein the oral product is a food product.

17. The method of claim 15, wherein the oral product is an oral care product.

18. The method of claim 15, wherein the oral product is a pharmaceutical product.

19. A water soluble composition, comprising:
a water soluble filler comprising *acacia* plant fibers in an amount of at least 90% w/w based on total weight of said composition as determined when said composition is in dry form; and
a natural sucrose substitute comprising an extract of *Stevia Rebaudiana*, the extract of *Stevia Rebaudiana* comprising at least about 95% rebaudioside A,
wherein said *acacia* plant fibers consist essentially of gum *acacia* plant fibers having a dietary fiber content of at least 85% w/w,
wherein, when the composition is in dry form, the natural sucrose substitute is present in an amount of from 0.03 gr to 0.05 gr per 1 gr of fiber gum and
wherein said composition does not comprise any of artificially produced sucrose substitutes.

20. A water soluble composition, comprising:
*acacia* plant fibers comprising fiber gum having a dietary fiber content of at least 85% w/w; and
an extract of *Stevia Rebaudiana*, the extract of *Stevia Rebaudiana* comprising at least about 95% rebaudioside A,
wherein, when the composition is in dry form, the extract of *Stevia Rebaudiana* is present in an amount of from 0.03 gr to 0.05 gr per 1 gr of fiber gum.

21. The water soluble composition of claim 20, wherein said composition does not comprise any artificially produced sucrose substitutes.

* * * * *